US009114098B2

(12) United States Patent
Moriyama et al.

(10) Patent No.: US 9,114,098 B2
(45) Date of Patent: Aug. 25, 2015

(54) METHOD FOR USING INACTIVATED JAPANESE ENCEPHALITIS VIRUS PARTICLES AS ADJUVANT

(75) Inventors: Makoto Moriyama, Kikuchi (JP);
Kazuyoshi Kaminaka, Kikuchi (JP);
Junichi Matsuda, Kikuchi (JP);
Chikateru Nozaki, Kikuchi (JP)

(73) Assignee: THE CHEMO-SERO-THERAPEUTIC RESEARCH INSTITUTE, Kumamoto (JP)

( * ) Notice: Subject to any disclaimer, the term of this patent is extended or adjusted under 35 U.S.C. 154(b) by 416 days.

(21) Appl. No.: 12/996,236

(22) PCT Filed: May 27, 2009

(86) PCT No.: PCT/JP2009/059671
§ 371 (c)(1),
(2), (4) Date: Dec. 3, 2010

(87) PCT Pub. No.: WO2009/147980
PCT Pub. Date: Dec. 10, 2009

(65) Prior Publication Data
US 2011/0081376 A1    Apr. 7, 2011

(30) Foreign Application Priority Data
Jun. 4, 2008    (JP) ................. 2008-147328

(51) Int. Cl.
*C07K 14/18* (2006.01)
*A61K 39/00* (2006.01)
(52) U.S. Cl.
CPC ......... *A61K 39/00* (2013.01); *A61K 2039/5252* (2013.01); *A61K 2039/55588* (2013.01)
(58) Field of Classification Search
None
See application file for complete search history.

(56) References Cited

U.S. PATENT DOCUMENTS

| 6,372,221 B2 * | 4/2002 | Mannhalter et al. ...... 424/196.11 |
| 2011/0020393 A1 * | 1/2011 | Komiya et al. ............. 424/201.1 |

FOREIGN PATENT DOCUMENTS

| CN | 1626242 | * | 6/2005 | ........... A61K 39/295 |
| CN | 1626242 A | | 6/2005 | |
| EP | 1 057 889 A1 | | 12/2000 | |
| EP | 1 123 711 A1 | | 8/2001 | |
| JP | 61-53227 | | 3/1986 | |
| JP | 8-231422 | * | 9/1996 | ........... A61K 39/295 |
| JP | 8-231422 A | | 9/1996 | |
| JP | 2000-83657 A | | 3/2000 | |
| JP | 2001-253833 A | | 9/2001 | |
| JP | 2004-65118 A | | 3/2004 | |
| JP | 2004-67696 A | | 3/2004 | |
| JP | 2007-231029 A | | 9/2007 | |
| JP | 2007-262097 A | | 10/2007 | |
| JP | 2008-231037 A | | 10/2008 | |
| KR | 10-2005-0008257 | | 1/2005 | |
| KR | 10-2005-0008257 A | | 1/2005 | |
| WO | WO 98/00167 A1 | | 1/1998 | |
| WO | WO 98/50071 A1 | | 11/1998 | |
| WO | WO 99/11762 A1 | | 3/1999 | |
| WO | WO 00/20565 A1 | | 4/2000 | |
| WO | WO 00/23107 A1 | | 4/2000 | |
| WO | WO 00/44758 A1 | | 8/2000 | |
| WO | WO 02/080965 A2 | | 10/2002 | |
| WO | WO 2006/085983 | * | 8/2006 | ............. A61K 48/00 |
| WO | WO 2009/082002 | * | 7/2009 | |

OTHER PUBLICATIONS

Srivastava et al (Vaccine 19:4557-4565, 2001).*
Schneerson et al. Infection and Immunity 52:519-528, 1986.*
Fattom et al. Infection and Immunity 58:2309-2312, 1990.*
Srivastava et al. (Vaccine. 2001; 19: 4557-4565).*
Kaltenbock et al. (Vaccine. May 2009; 27: 4483-4489).*
Kikukawa et al. (Vaccine. 2012; 30: 2329-2335).*
Takeshita et al. (Journal of Infection and Chemotherapy. 2014; 20: 238-242).*
Yun et al. (BMC Infectious Diseases. Jan. 2015; 15 (7): 1-11).*
Eiji Konishi, "Increase in the Neutralizing Antibody Induction Ability of the Dengue Tetravalent DNA Vaccine in Mice by Administrating with Protein Vaccine", Health and Labour Sciences Research Grant, Division Research Report, 2006, pp. 70-77.
(Disclosed Anonymously), "Polyvalent Antigen Vaccine for Human Use", Research Disclosure No. 329, Sep. 1991, p. 32975.
Combined Chinese Office Action and Search Report issued Sep. 6, 2012, in Patent Application No. 200980130727.9 (with English-language translation).
Extended European Search Report issued Mar. 26, 2013, in European Patent Application No. 09758247.2.
Eiji Mutoh, et al., "Japanese encephalitis subunit vaccine composed of virus-like envelope antigen particles purified from serum-free medium of a high-producer J12#26 cell clone", Vaccine, vol. 22, No. 20, XP-004515439, Jun. 30, 2004, pp. 2599-2608.
David W. C. Beasley, et al., "Protection against Japanese encephalitis virus strains representing four genotypes by passive transfer of sera raised against ChimeriVax™—JE Experimental vaccine", Vaccine, vol. 22, No. 27-28, XP-004526953, Sep. 9, 2004, pp. 3722-3726.

(Continued)

*Primary Examiner* — Shanon A Foley
(74) *Attorney, Agent, or Firm* — Oblon, McClelland, Maier & Neustadt, L.L.P.

(57) ABSTRACT

A method for using inactivated Japanese encephalitis virus particles as an adjuvant of a vaccine is provided. A method for using inactivated Japanese encephalitis virus (JEV) particles as an adjuvant of various vaccines or a mixed vaccine, said JEV particles being obtained by inoculating JEV Beijing-1 strain to Vero cells, culturing said JEV-infected cells to give cultured cells or culture supernatant, purifying JEV particles from said cultured cells or culture supernatant and inactivating said JEV particles with formalin, a method for preparing a (mixed) vaccine which comprises a step of letting inactivated Japanese encephalitis virus be contained, and a mixed vaccine prepared by said method.

16 Claims, 6 Drawing Sheets

(56) References Cited

OTHER PUBLICATIONS

Eiji Konishi, "Increase in the Neutralizing Antibody Induction Ability of the Dengue Tetravalent DNA Vaccine in Mice by Administrating with Protein Vaccine", Health and Labour Sciences Research Grant, Division Research Report, 2006, pp. 70-77. (Partial English Translation only (previously filed on Feb. 8, 2011 in IDS without English translation)).

* cited by examiner

METHOD FOR USING INACTIVATED JAPANESE ENCEPHALITIS VIRUS PARTICLES AS ADJUVANT

TECHNICAL FIELD

The present invention relates to a method for using inactivated Japanese encephalitis virus (hereinafter also referred to as "JEV") particles as an adjuvant for various mixed vaccines or polyvalent vaccines.

BACKGROUND ART

Vaccination to infectious diseases should preferably be finished by infancy. For this purpose, many kinds of vaccines need to be inoculated in a fixed period of time. As a devise for efficient vaccination to various infectious diseases, mixed vaccines in which several vaccines are mixed together have been developed. A mixed vaccine has many merits including: (i) it may provide protection to plural pathogens simultaneously, (ii) it may eliminate troublesomeness of inoculation schedule of plural vaccinations, (iii) it may reduce a cost for vaccinations (technical fee) and burden of time for individuals who receive vaccinations with increase in a vaccination rate being expected, (iv) it may reduce burden of medical staff, and (v) it may reduce burden to environments by diminution of waste materials through reduction of vaccination frequency. Thus, for a mixed vaccine, the more vaccine antigens are contained therein, the better.

However, the number of vaccine antigens to be mixed together for preparing a mixed vaccine is limited. Namely, the larger number of vaccine antigens are mixed, the less an amount of each of the vaccine antigens can be administered. Besides, some kinds of antigens may interfere with each other to thereby lead to reduction of their antibody-inducing capacity, which may result in reduction in antibody titer of a vaccine and make efficient protection against infection difficult.

Concrete mixed vaccines that have been published up till the present include a diphtheria/pertussis/tetanus (DPT) mixed vaccine preparation "VACCINE COMPOSITION" (cf. e.g. Patent reference 1), a mixed vaccine containing papilloma virus (HPV) antigen "Novel Composition" (cf. e.g. Patent reference 2), a polyvalent DTP polio vaccine "MULTIVALENT DTP-POLIO VACCINES" (cf. e.g. Patent reference 3), a method for inducing cellular immune activity of a live vaccine in an inactivated vaccine and a mixed vaccine obtained by said method (cf. e.g. Patent reference 4), and the like. In addition to these, mixed vaccines of numerous combinations have already been published. For a Japanese encephalitis virus vaccine, mixed vaccines with DTP vaccine, hepatitis B vaccine (HepB), hepatitis A vaccine (HepA), and the like have been reported (cf. e.g. Non-patent reference 1). Development of a mixed vaccine with more combinations is desired but there is the problem of reduced effect of a vaccine as described above. In order to solve the problem, development of such an adjuvant that allows for a higher antibody titer with as little amount of an antigen as possible is desired.

In general, an adjuvant, when added to a vaccine antigen, is known to enhance immunogenicity of the vaccine antigen and includes an aluminum gel particle (aluminum salt), an oil adjuvant comprising a mineral oil as a main component, a surfactant-like adjuvant such as saponin purified from white hyacinth bean, and a TH1-inducing adjuvant derived from intracellular toxins (LPS, etc.). For an adjuvant for use in a vaccine for animal, an oil adjuvant may be often used which is locally more reactive than an aluminum adjuvant. For an adjuvant to be used in a vaccine for human, however, safety is required in addition to efficacy.

For an adjuvant to be used in a vaccine for human, an aluminum gel has hitherto been used primarily as its efficacy has been proved but recently newly developed MPL and double-stranded RNA have got to be chosen for use. Already known adjuvant compositions include "Vaccine" consisting of an immunostimulating agent (MPL) and a metal salt (cf. e.g. Patent reference 5), an oil-in-water emulsion "Adjuvant composition" (cf. e.g. Patent reference 6) which comprises oil such as 3D-MPL, squalene, alpha-tocopherol, polyoxyethylene sorbitan monooleate, and the like, a synthetic compound adjuvant "Immunologic adjuvant compound" (cf. e.g. Patent reference 7), "Vaccine preparation" (cf. e.g. Patent reference 8) which utilizes cholera toxin, "Use of virus-like particle as adjuvant" (cf. e.g. Patent reference 9) which utilizes virus-like particle (VLP) formed from a particle-forming polypeptide of a surface antigen of hepatitis virus, and many others.

For Japanese encephalitis virus vaccine, an inactivated vaccine is currently used which is prepared by inoculating Japanese encephalitis virus (JEV) into the brain of mice, purifying the virus from the brain with symptoms of encephalitis, and inactivating the virus with formalin. Inactivated JEV vaccines using African green monkey kidney epithelial (Vero) cells in place of the brain of mice have been developed (cf. e.g. Patent references 10, 11 and 12). However, it was not known that these JEV particles have an adjuvant activity.

Patent reference 1: WO2002/080965
Patent reference 2: Japanese patent publication No: 2004-67696
Patent reference 3: WO98/00167
Patent reference 4: Japanese patent publication No: 2001-253833
Patent reference 5: Japanese patent publication No: 2007-262097
Patent reference 6: Japanese patent publication No: 2007-231029
Patent reference 7: Japanese patent publication No: 2002-535411
Patent reference 8: WO00/23107
Patent reference 9: WO98/08146
Patent reference 10: WO00/20565
Patent reference 11: Japanese patent publication No: 2000-83657
Patent reference 12: Japanese patent publication No: 2004-65118
Non-patent reference 1: RESEARCH DISCLOSURE no. 329, September 1991, HAVANT GB 'POLYVALENT ANTIGEN VACCINE FOR HUMAN USE' 32975

DISCLOSURE OF THE INVENTION

Technical Problem to be Solved by the Invention

As described above, while development of a mixed vaccine is desired as enabling immunization to more infectious diseases at a stretch, the larger number of vaccine antigens are mixed, the less an amount of each of the vaccine antigens is forced. Thus, in order to make up for this drawback, development of such an adjuvant that allows for a higher antibody titer even with a lower amount of an antigen is desired.

Means for Solving the Problems

Under the circumstances, the present inventors have earnestly continued research activities and as a result have found that, by adding inactivated JEV particles to a vaccine solution containing all or a portion of protective antigens to infectious diseases, i.e. diphtheria, pertussis, tetanus, polio, hepatitis B and hepatitis A, immunization was induced at a higher level and more rapidly as compared to the corresponding vaccine solution not containing said inactivated JEV particles, namely, that the inactivated JEV particles do possess the activity as an adjuvant, and thus completed the present invention. Up till the present invention, there was no idea to utilize the adjuvant activity exerted by the inactivated JEV particles per se, the inactivated JEV particles being a vaccine antigen of a mixed vaccine. The idea the present inventors have firstly found out. An object of the present invention is to provide a method for using inactivated JEV particle as an adjuvant for various mixed vaccines and a mixed vaccine containing the JEV.

Accordingly, the present invention is as follows:
(1) A method for using inactivated Japanese encephalitis virus as an adjuvant of a vaccine.
(2) The method of (1) above wherein the inactivated Japanese encephalitis virus is one obtained by inactivating Japanese encephalitis virus obtained by cell culture.
(3) The method of (1) or (2) above wherein the inactivated Japanese encephalitis virus has a particle-like structure.
(4) The method of any one of (1) to (3) above wherein the vaccine is a mixed vaccine.
(5) A method for preparing a vaccine which comprises a step of letting inactivated Japanese encephalitis virus be contained as an adjuvant.
(6) The method of (5) above wherein the inactivated Japanese encephalitis virus is one obtained by inactivating Japanese encephalitis virus obtained by cell culture.
(7) The method of (5) or (6) above wherein the inactivated Japanese encephalitis virus has a particle-like structure.
(8) The method of any one of (5) to (7) above wherein said step is a step of adding the inactivated Japanese encephalitis virus to a vaccine.
(9) The method of any one of (5) to (8) above wherein the vaccine is a mixed vaccine in which two or more different vaccines are mixed together.
(10) The method of (9) above wherein said vaccine is selected from the group consisting of a diphtheria vaccine, a pertussis vaccine, a tetanus vaccine, a polio vaccine, a hepatitis A vaccine, a hepatitis B vaccine, a rabies vaccine, a measles vaccine, a rubella vaccine, an influenza vaccine, a mumps vaccine, a varicella vaccine, a rota vaccine, a smallpox vaccine, a yellow fever vaccine, a mite-mediated encephalitis vaccine, an Hib vaccine, a typhoid vaccine, a cholera vaccine, a BCG vaccine, a pneumococcus vaccine and a vaccine against meningitis caused by *Neisseria meningitidis*.
(11) The method of any one of (5) to (10) above wherein the inactivated Japanese encephalitis virus particles are at 250 ng to 34 µg/mL.
(12) A vaccine prepared by the method of any one of (5) to (11) above.
(13) The vaccine of (12) above which comprises an aluminum adjuvant.

More Efficacious Effects than Prior Art

According to the present invention, a method for preparing a vaccine comprising inactivated JEV particles as an adjuvant and a vaccine prepared by said method are provided. For instance, by adding inactivated JEV particles to a mixed vaccine as an adjuvant, immunization may be induced at a higher level and more rapidly as compared to the corresponding vaccine with no addition of said inactivated JEV particles. Namely, since a given antibody titer capable of attaining protection against infection may be obtained with a smaller amount of an antigen, an amount of each of antigens to be contained in a mixed vaccine may be reduced to thereby allow for more kinds of antigens be contained in a mixed vaccine.

Besides, in accordance with the method of the present invention, not only immunization of a mixed vaccine may be exerted but also an antibody titer for preventing infection of Japanese encephalitis virus may be increased. Thus the mixed vaccine of the invention is also used as a Japanese encephalitis vaccine.

BEST MODE FOR CARRYING OUT THE INVENTION

The present invention is characterized by a method for preparing a vaccine which comprises a step of adding inactivated JEV as an adjuvant.

JEV strains for use herein may be any with no specific limitation. Beijin-1 strain was used for the invention. JEV may be obtained by two methods as described hereinbelow. One is a method where JEV is inoculated in the brain of mice and the viruses are propagated in the brain and then purified therefrom. The other is a method where JEV is inoculated in culture cells, the virus-infected cells are cultured and the viruses are purified from the grown JEV-infected cells and culture supernatant. From the viewpoint of animal protection, the method with propagation with the culture cells is preferable. For a host cell for propagation of JEV, Vero cells may be used that allows for good propagation of JEV and production of an antigen with higher antigenicity. A culture medium for expansion culture of cells may suitably be selected from one commonly used for tissue culture such as M199 medium, Eagle MEM medium, and the like, preferably Dulbecco MEM medium optionally supplemented with an amino acid, salts, an anti-mold/anti-bacterial agent, animal serum, and the like. A high-density culture using a microcarrier may sometimes be carried out for obtaining a large amount of JEV particles. A number of microcarriers for this purpose are known. A microcarrier suitable for growth of Vero cells includes Cytodex (Cytodex I, Amersham Pharmacia Biotech) at a concentration of 5 g/L or less.

Culture temperature and duration of culture may be adjusted depending on a combination of the cell types, an amount of viruses inoculated, a scale and procedure of culture, and the like. For instance, when JEV is propagated by static culture or roller bottle culture with Vero cells, the cells may be cultured in a growth medium consisting of Dulbecco MEM medium supplemented with a non-essential amino acid and bovine serum at a culture temperature of 32° C. to 38° C. for duration of culture of 2 to 7 days. For propagation of JEV, the culture medium is removed by aspiration when the growth reached stable stage and, after washing with a phosphate buffer/saline several times, JEV is inoculated to the cells at multiplicity of infection (M.O.I) of 0.01 to 0.0001. For a maintenance medium used after viral inoculation, a serum-free, low-protein level medium may preferably be used. For instance, VP-SFM (GIBCO) supplemented with L-glutamic acid may be used. The cells may be cultured at the culture temperature as described above for 4 to 7 days. After completion of culture, the resultant culture, i.e. cell-breakage solution or culture supernatant, may be recovered, added with formalin and left to stand at around 4° C. for 1 to 3 months or more to inactivate the viruses.

For purification of JEV particles from the obtained JEV-containing solution, purification procedures commonly used in protein chemistry may be used, e.g. centrifugation, salting-out, normal filtration, ultrafiltration, isoelectric precipitation, electrophoresis, ion exchange chromatography, gel filtration chromatography, affinity chromatography, hydrophobic chromatography, hydroxyapatite chromatography, and the like. Among these, suitable procedure may be selected and used in combination thereof. In the Examples herein, JEV particles were purified by subjecting the JEV-containing solution to sucrose-gradient centrifuge, fractionating and pooling fractions of JEV particles, and performing affinity chromatography with cellulose sulfate ester gel. The solution containing the inactivated JEV after purification may be diluted with e.g. a phosphate buffer or saline to a viral content suitable for use as an adjuvant. The thus obtained solution containing the inactivated JEV particles may be added to various vaccines as an adjuvant.

The method of the present invention may be used for either a vaccine against viral infectious diseases or for a vaccine against bacterial infectious diseases. A vaccine against viral infectious diseases includes, for instance, a vaccine against hepatitis A, hepatitis B, rabies, polio, measles, rubella, influenza, yellow fever, mite-mediated encephalitis, mumps, varicella, rota, smallpox, and the like. A vaccine against bacterial infectious diseases includes, for instance, pertussis, diphtheria, tetanus, typhoid, cholera, meningitis caused by *Neisseria meningitidis*, Hib (*Haemophilus influenzae* type b), BCG, pneumococcus, and the like. A vaccine selected from these may be used solely or may be a mixed vaccine in which two or more vaccines are mixed together. However, since an amount of an antigen to be contained in a vaccine may be reduced when inactivated JEV particles are used as an adjuvant, the vaccine may preferably be used as a mixed vaccine where an amount of antigens is restricted.

Dosage form may be injections, syringes, transdermal agents, and sprays, with the vaccine being a liquid preparation in which liquid-liquid products have already been mixed in a bulking step, a systemic preparation in which a liquid-liquid product and a liquid-lyophilized product are put in containers for one-touch mixing when use, or a preparation in which a liquid-liquid product and a liquid-lyophilized product are mixed manually when use. A route of administration includes intramuscular injection, subcutaneous injection, transdermal administration, and the like, which may suitably be selected depending on purposes. A route of administration may also be such that either the same site of administration or different sites of administration may be used.

For the vaccines described above, a suitable adjuvant may be added to an antigen solution for enhancing immunogenicity. An amount of an adjuvant to be added may suitably be set depending on the kind, the number and an amount of an antigen. The kind of an adjuvant includes aluminum hydroxide gel, aluminum phosphate gel, aluminum sulfate gel, mineral oil, non-mineral oil, and the like. An aluminum gel, which has been used for a number of vaccine for human and well proved to be safe, is mostly used. Although an aluminum gel is proved to be safe, if its dose is not observed, adverse side effects such as aluminum encephalopathy or aluminum bone disease may be seen. Therefore, an aluminum gel may preferably be used at as low an amount as possible. Since the inactivated JEV particles in accordance with the present invention allow for reduction of an amount of an aluminum gel in an aluminum-containing vaccine, the vaccine of the present invention may effectively be used in combination with an aluminum gel.

The inactivated JEV particles may be used at a range of 250 ng to 34 µg/mL where the adjuvant activity is exerted, preferably at 1 to 16 µg/mL, more preferably at 2 to 8 µg/mL. For schedule of addition of the inactivated JEV particles to a vaccine, the inactivated JEV particles may be added while or after said vaccine is prepared. For instance, a suitable amount of the inactivated JEV particles may be added to a stock solution of an attenuated live vaccine or a stock solution of an inactivated vaccine or a mixture thereof and then the solution may suitably be diluted with a phosphate buffer or saline. Before addition of the inactivated JEV particles, an aluminum gel may be used as occasion demands. The vaccine and an aluminum gel may be used at a range of 50 ng to 80 µg/mL and at 100 to 400 µg/mL, respectively.

Evaluation of the inactivated JEV particles as an adjuvant may be done by comparing immune response induced when a vaccine or a mixed vaccine containing the inactivated JEV particles is injected to animals via subcutaneous, intramuscular or intradermal administration with immune response induced when the vaccine not containing the inactivated JEV particles is injected to the animals. For the evaluation, a small animal such as rat, mouse, guinea pig or rabbit may be used. For instance, animals immunized with a vaccine containing the inactivated JEV particles may be bled, serum be isolated therefrom and an antibody (titer) in the obtained serum be measured for comparison with an antibody (titer) in serum from animals immunized with a vaccine not containing the inactivated JEV particles to thereby evaluate the inactivated JEV particles as an adjuvant. A method for measuring an antibody (titer) includes ELISA, EIA, a neutralization test with a toxin and cell line, and the like, any of which may be used.

The present invention is explained in more detail by means of the following Reference Examples and Examples but should not be construed to be limited thereto.

REFERENCE EXAMPLE 1

Japanese encephalitis virus particles were prepared as described in Japanese patent publication No. 2000-83657. Briefly, Japanese encephalitis virus (Beijin-1) at M.O.I. of 0.01 was inoculated to Vero cells grown by suspension culture with Dulbecco MEM medium and, after absorption at 37° C. for 90 minutes, the cells were cultured at the same temperature for 3 to 5 days while supplementing the medium. The culture solution was subjected to a sucrose-gradient centrifuge to recover viral fractions and the virus particles were purified by cellulose sulfate ester gel. For inactivation of the virus particles, the virus particles were left to stand under conditions of 0.08 vol % formalin in a refrigerator for about half a year. The thus obtained inactivated Japanese encephalitis virus particles were used in Examples. An amount of protein in the inactivated Japanese encephalitis virus particles was measured by Lowry method.

REFERENCE EXAMPLE 2

(1) Elisa used for measurement of antibody titer

For an immobilized antigen, pertussis toxoid (PT) at 2.5 µg/mL, diphtheria toxoid (DT) at 5 µg/mL, tetanus toxoid (TT) at 5 µg/mL, hepatitis B virus surface antigen (HBs) at 5 µg/mL, poliovirus type 1 at 1.9 Du/mL, poliovirus type 2 at 0.975 Du/ml, poliovirus type 3 at 1.5 Du/mL, and inactivated JEV particles at 5 µg/mL. For HBs and inactivated JEV particles, an amount of protein was measured by Lowry method. For each of DTP, an amount of protein nitrogen was measured by Kjeldahl method and converted to an amount of protein. For poliovirus, an amount of D antigen was measured. An antigen to be immobilized was added to a 96-well plate (Nunc, Maxisorp) at 100 µL/well and the plate was left to stand at 4° C. overnight for immobilization. On the next day, each well was washed three times with 350 µL of PBS containing 0.05% Tween 20 (PBST) and added with 350 µL/well of Block Ace (Dainippon Sumitomo Pharma Co., Ltd., hereinafter abbreviated to "BA") diluted 4-fold with PBS and the plate was left to stand at room temperature for 2 hours. After 2 hours, 4-fold diluted BA was removed sufficiently and the wells were washed three times with 350 µL/well of PBST. Then, samples were diluted with BA diluted 10-fold with PBS containing 0.05% Tween 20 and each 100 µL/well of the diluted samples was added. After reaction at 37° C. for 2 hours, the wells were washed three times with 350 µL/well of PBST. After the washing solution was removed sufficiently, each 100 µL/well of HRP-labeled anti-mouse IgG goat antibody (American Qualax, A131PS) or HRP-labeled anti-mouse IgG rat antibody (Zymed, 04-6020), HRP-labeled anti-rat IgG (H+L) goat antibody (Zymed, 81-9520), each diluted 2000-fold with the solution used for dilution of the samples, was added to the wells for reaction at 37° C. for 1 hour. After 1 hour, the solution was discarded sufficiently and the wells were washed with 350 µL/well of PBST four times and with the same amount of distilled water twice. A chromogenic substrate TMB+(Dako) was added at 100 µL/well for reaction under shading at room temperature for 30 minutes. Then, 1 N sulfuric acid was added at 100 µL/well to stop development and absorbance at 450 nm was measured.

(2) Preparation of Standard Serum and Calculation of Antibody Titer

Serum, where a sufficient antibody titer was proved by the antibody titer measuring system as described below two to four weeks after immunization of an animal with an antigen for protection against an infectious disease, was used as standard serum. By way of example, standard serum to each of DTP antigens was one bled from an animal immunized for 2 weeks with intraperitoneal administration of 0.5 mL of the current DTP preparation diluted 5-fold. For an antibody titer of the respective antigens, sera from 26 to 30 mice not immunized were diluted 50-fold or 200-fold with a dilution solution for samples and each of the diluted samples in duplicate were subject to ELISA as described above to measure OD 450 nm. A mean value of the measured OD 450 nm plus two times standard deviation was set for a cut-off. The standard sera were serially diluted and OD 450 nm was measured. Dilution fold in excess of the cut-off value (PT: 12,800-fold, DT: 96,000-fold, TT: 320,000-fold, JEV: 1,024,000-fold) was used as an antibody titer of standard serum. Namely, serum at the dilution fold was set as 1 EU of the respective antibody titer for measurement of the samples. For ELISA of anti-poliovirus antibody, a sample diluted 100-fold was used for measurement of OD.

(3) Measurement of Antibody Titer of Anti-HBs Antibody and Determination of Rate of Change to Positive For anti-HBs antibody titer, not only ELISA but also IMx Ausab Assay System (abbott, 2262-83) were used to measure antibody titer and a rate of change to positive.

EXAMPLE 1

Adjuvant Activity of JEV Particles to DTP Vaccine Antigen

The inactivated Japanese encephalitis virus (JEV) particles obtained in Reference Example 1 and each antigens of DTP were mixed together in a composition as shown in Table 1. The obtained mixture (0.5 mL) was inoculated intraperitoneally to SPF mice (C57BL/6s; 4 mice/group) of 10 weeks old (male). The animals were bled before inoculation and on Week 2, 3, and 4 after primary inoculation. After bleeding at Week 4, booster was administered with the same mixture. The animals were bled on Week 1 and 2 after the second inoculation and antibody titer of the respective sera was measured in accordance with the method for measurement of antibody titer as described in Reference Example 2-(1). As a result, negative interference of antigens to each other due to addition of JEV was not observed. It was found that an antibody titer to the respective antigens of DTP (PT, DT, TT) in the group with addition of JEV was higher than that in the group with DTP alone (FIGS. 1*a, b, c*). The adjuvant activity of JEV particles could be seen on Week 2 after primary inoculation.

TABLE 1

| | DTP vaccine | JEV particles |
|---|---|---|
| Group 1 | PT: 0.24 μg/head, DT: 0.41 Lf/head, | — |
| Group 2 | TT: 0.043 Lf/head, Alum: 0.006 mg/mL | 1 μg/head |

EXAMPLE 2

Effect of Concentration of JEV Particles on Adjuvant Activity (1) The JEV particles obtained in Reference Example 1 and each antigens of DTP were mixed together in a composition as shown in Table 2. The obtained mixture (0.5 mL) was inoculated intraperitoneally to SPF mice (C57BL/6s; 5 mice/group) of 9 weeks old (male). The animals were bled before inoculation and on Week 4 after primary inoculation. Antibody titer of the respective sera was measured in accordance with the method for measurement of antibody titer as described in Reference Example 2-(1). The outcomes of the measurement of antibody titer are shown in a geometrical mean. As a result, it was found that an antibody titer to the respective antigens of DTP (PT, DT, TT) in Groups 2 to 7 was higher than that in Group 1 where the JEV particles were not added (FIG. 2).

TABLE 2

| Group | DTP vaccine | JEV particles |
|---|---|---|
| 1 | PT: 0.24 µg/head, | — |
| 2 | DT: 0.41 Lf/head, | 0.25 µg/head |
| 3 | TT: 0.043 Lf/head, | 0.5 µg/head |
| 4 | Alum: 0.006 g/mL | 1 µg/head |
| 5 | | 2 µg/head |
| 6 | | 4 µg/head |
| 7 | | 8 µg/head |

Figure 1:
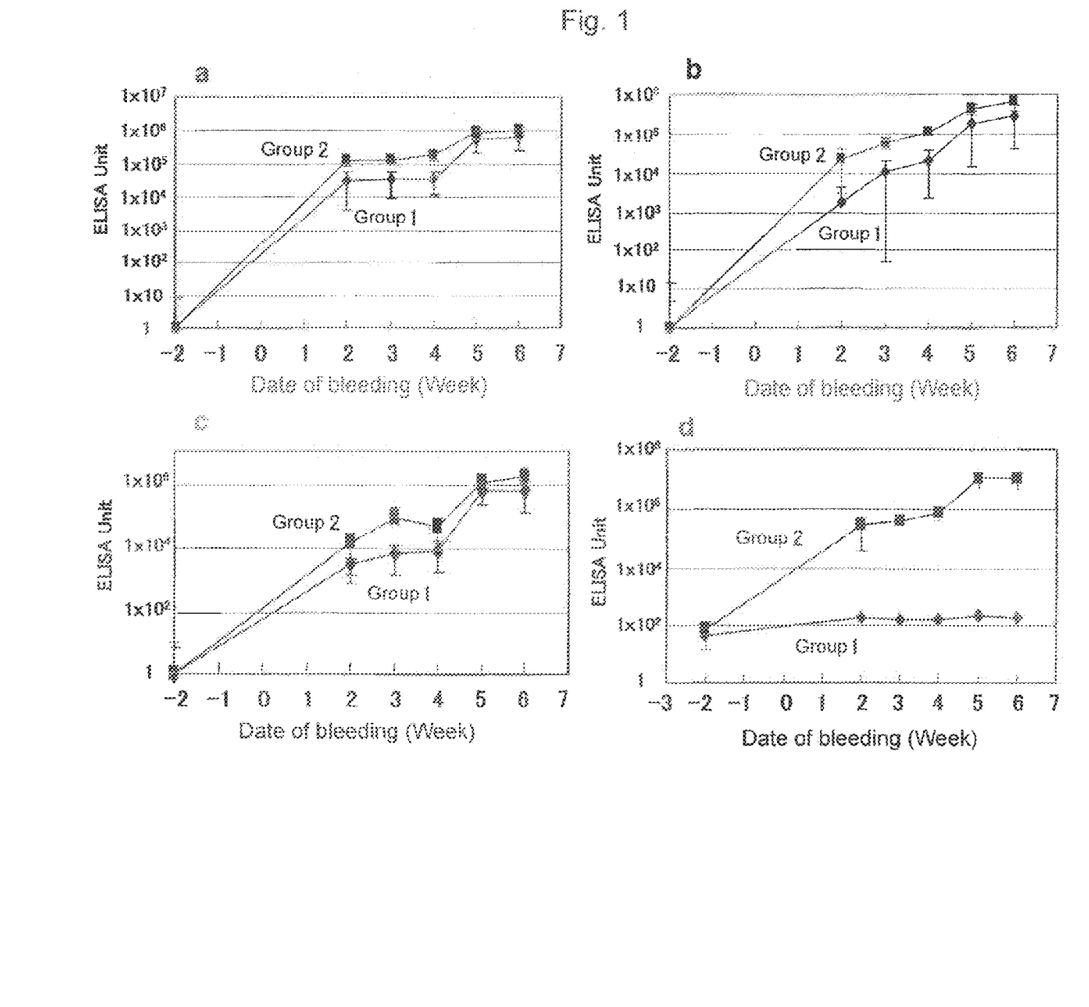
FIG. 1 shows the results of ELISA carried out on sera from mice immunized with a mixture of a DTP vaccine and JEV particles. a: Anti-TT antibody titer; b: Anti-PT antibody titer; c: Anti-DT antibody titer; d: Anti-JEV antibody titer
Figure 2:
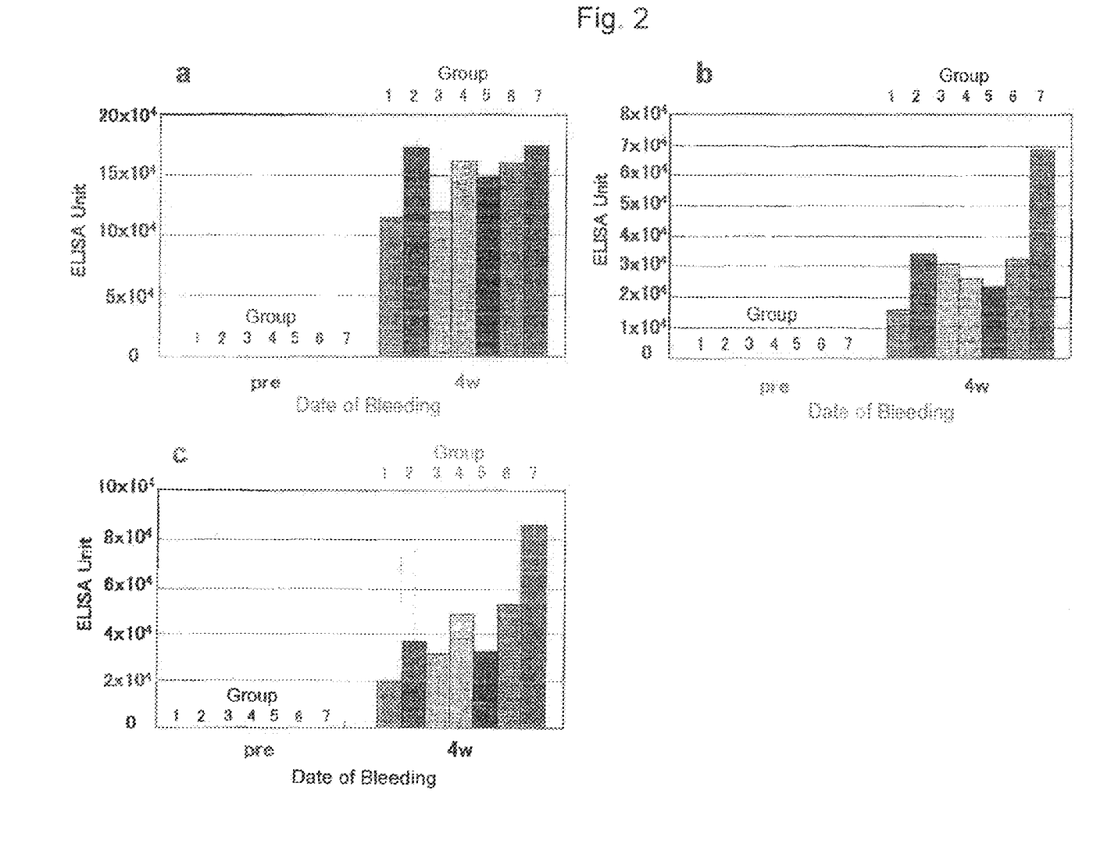
FIG. 2 shows the results of ELISA carried out on sera from mice immunized with a mixture of a DTP vaccine and JEV particles at various concentrations. a: Anti-TT antibody titer; b: Anti-PT antibody titer; c: Anti-DT antibody titer
Figure 3:
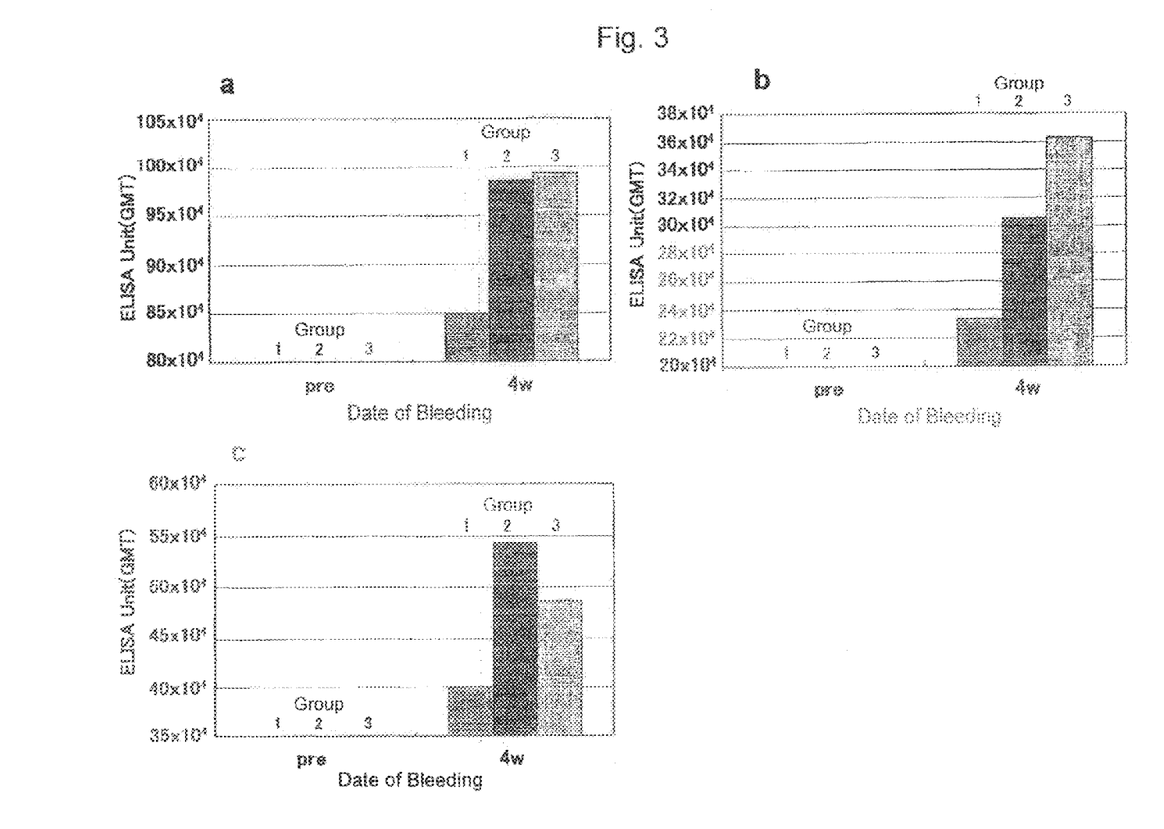
FIG. 3 shows the results of ELISA carried out on sera from mice immunized with a mixture of a DTP vaccine and JEV particles at various concentrations. a: Anti-TT antibody titer; b: Anti-PT antibody titer; c: Anti-DT antibody titer

(2) The JEV particles obtained in Reference Example 1 and each antigens of DTP were mixed together in a composition as shown in Table 3. The obtained mixture (0.5 mL) was inoculated intraperitoneally to BDF-1 mice (4 mice/group) of 9 weeks old (female). The animals were bled before inoculation and on Week 4 after primary inoculation. Antibody titer of the respective sera was measured in accordance with the method for measurement of antibody titer as described in Reference Example 2-(1). It was found that an antibody titer in Groups with addition of the JEV particles was higher than that in Group with no addition of the JEV particles (FIG. 3).

TABLE 3

| Group | DTP vaccine | JEV particles |
|---|---|---|
| 1 | PT: 3.6 µg/head, DT: 6.25 | — |
| 2 | Lf/head, TT: 0.65 Lf/head, Alum: | 1 µg/head |
| 3 | 0.1 mg/mL | 8 µg/head |

EXAMPLE 3

Adjuvant Activity of JEV Particles to IPV Vaccine

Figure 4:
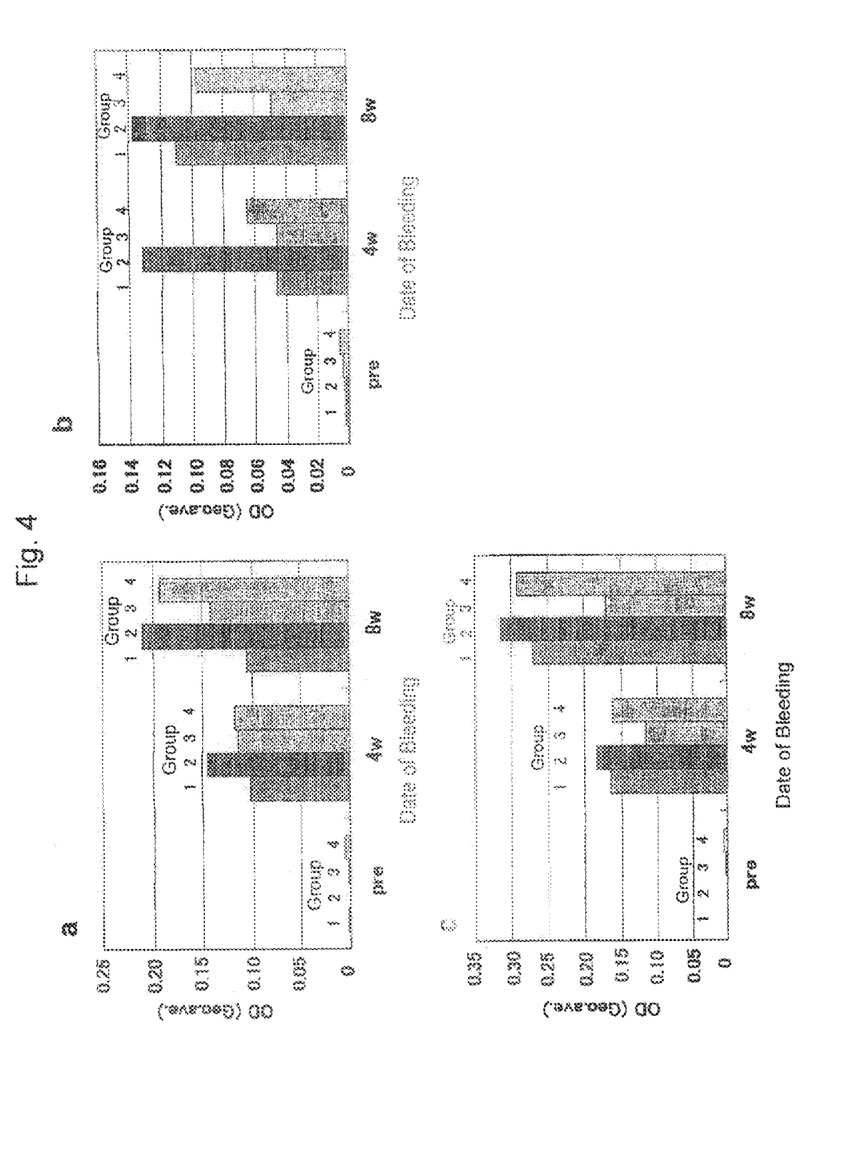
FIG. 4 shows the results of ELISA carried out on sera from rats immunized with a mixture of a IPV vaccine and JEV particles. a: Anti-PV-1 antibody titer; b: Anti-PV-2 antibody titer; c: Anti-PV-3 antibody titer

The JEV particles obtained in Reference Example 1 and the commercially available IPV vaccine (IMOVAX POLIO Sanofi Pasteur) diluted 2-fold and 4-fold were mixed together in a composition as shown in Table 4. The obtained mixture (0.5 mL) was intramuscularly injected to SPF rats (Wister; 3 rats/group) of 8 weeks old (female) at the thigh of hind leg. The animals were bled before inoculation and on Week 4 and 8 after primary inoculation. Antibody titer of the respective sera was measured in accordance with the method for measurement of antibody titer as described in Reference Example 2-(1). It was found that an antibody titer in Groups with addition of the JEV particles was higher than that in Group with no addition of the JEV particles (FIG. 4).

TABLE 4

| Group | IPV vaccine | JEV particles |
|---|---|---|
| 1 | 2-fold dilution | — |
| 2 | (I: 20 UD, II: 4 UD, III: 16 UD) | 1 µg/head |
| 3 | 4-fold dilution | — |
| 4 | (I: 10 UD, II: 2 UD, III: 8 UD) | 1 µg/head |

EXAMPLE 4

Adjuvant Activity of JEV Particles to HepB Vaccine

Figure 5:
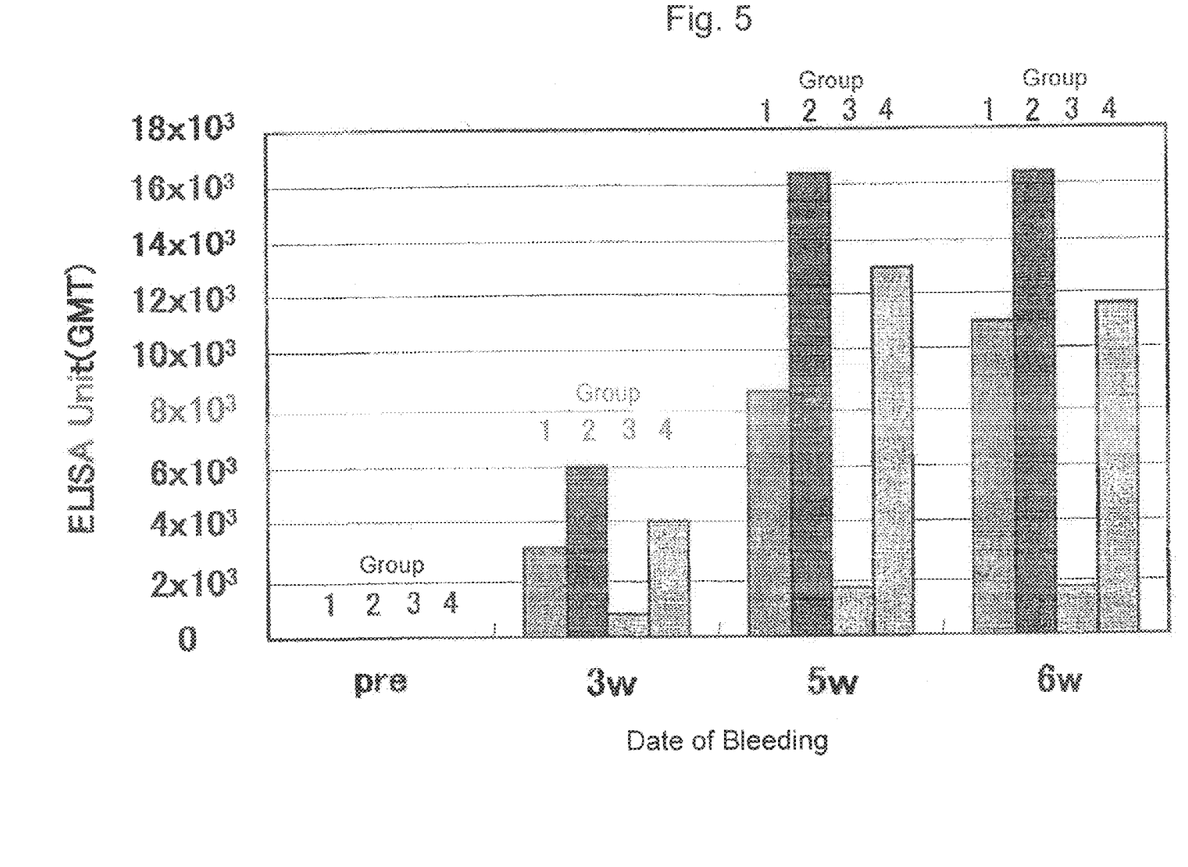
FIG. 5 shows the results of ELISA carried out on sera from mice immunized with a mixture of a HepB vaccine and JEV particles (Anti-HBs antibody titer).
Figure 6:
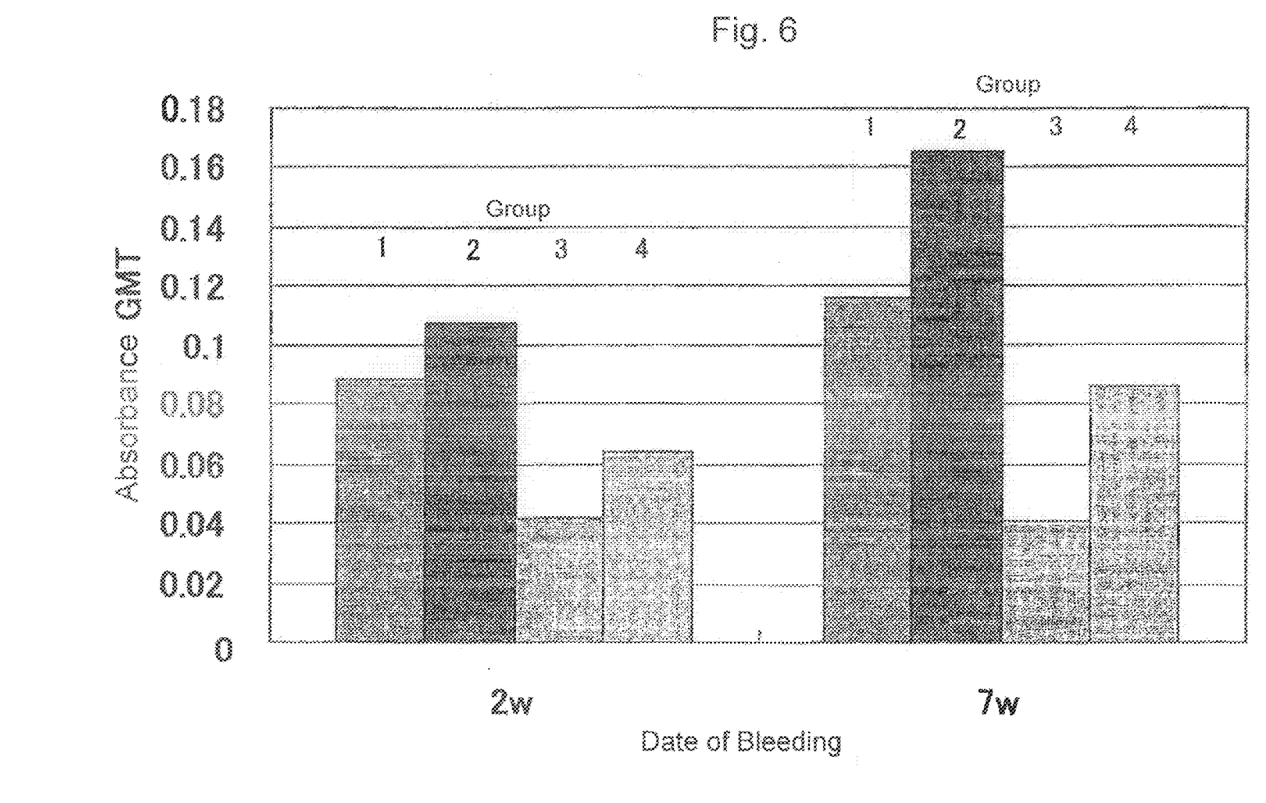
FIG. 6 shows the results of ELISA carried out on sera from mice immunized with a mixture of an HepA vaccine and JEV particles (Anti-HVA antibody titer).

The JEV particles obtained in Reference Example 1 and HBs antigen of HepB vaccine were mixed together in a composition as shown in Table 5. The obtained mixture (1 mL) was inoculated intraperitoneally to BALB/c (5 mice/group) of 5 weeks old (male). The animals were bled before inoculation and on Week 3, 5 and 6 after primary inoculation. Antibody titer of the respective sera was measured in accordance with the method for measurement of antibody titer as described in Reference Example 2-(1). It was found that an antibody titer in Groups with addition of the JEV particles was higher than that in Group with no addition of the JEV particles (FIG. 5). When JEV was added to HepB vaccine at the dose of 0.25 µg/head, antibody titer was recovered to the same or more level of HepB vaccine at the dose of 0.5 µg/head. Antibody titer of the respective sera was also measured in accordance with the method as described in Reference Example 2-(3). Group 4 with addition of the JEV particles showed a higher rate of change to positive than Group 3 with no addition of the JEV particles (Table 6).

TABLE 5

| Group | HepB vaccine | JEV particles |
|---|---|---|
| 1 | HBs: 0.5 μg/head, | — |
| 2 | Alum: 0.01 mg/mL | 1 μg/head |
| 3 | HBs: 0.25 μg/head, | — |
| 4 | Alum: 0.006 mg/mL | 1 μg/head |

TABLE 6

| Group | Mean antibody titer (mIU/mL) | Rate of change to positive |
|---|---|---|
| 1 | 80 | 100% (5/5) |
| 2 | 118 | 100% (5/5) |
| 3 | 26 | 60% (3/5) |
| 4 | 19 | 80% (4/5) |

EXAMPLE 5

Adjuvant Activity of JEV Particles to HepA Vaccine

The JEV particles obtained in Reference Example 1 and HAV antigen of HepA vaccine were mixed together in a composition as shown in Table 7. The obtained mixture (1 mL) was inoculated intraperitoneally to BALE/c (5 animals/group) of 5 weeks old (male). The animals were bled before inoculation and on Week 2 and 7 after primary inoculation. Antibody titer of the respective sera was measured by ELISA. For a primary solid phase, anti-HAV rabbit antiserum was used. After washing three times with PEST, an HAV antigen was immobilized at 1.25 ng/50 μL/well. Samples were applied for reaction at 4° C. overnight. After washing three times with PBST, a secondary antibody with HRP conjugate was reacted. After washing four times with PEST, a substrate was reacted and absorbance was measured. The measurement was also done for 30 samples of non-immunized sera, a cut-off (3SD) was calculated and a rate of change to positive was obtained (2 w cut-off: 0.061, 7 w cut-off: 0.065).

It was found that an antibody titer in Groups with addition of the JEV particles was higher than that in Group with no addition of the JEV particles (FIG. 6). There was distinction in a rate of change to positive between Groups 1 and 2 on Week 2 after inoculation and between Groups 3 and 4 on Week 2 and 7 after inoculation (Table 8).

TABLE 7

| Group | HepA vaccine | JEV particles |
|---|---|---|
| 1 | HAV antigen: | — |
| 2 | 0.05 μg/head | 1 μg/head |

TABLE 7-continued

| Group | HepA vaccine | JEV particles |
|---|---|---|
| 3 | HAV antigen: | — |
| 4 | 0.025 µg/head | 1 µg/head |

TABLE 8

| | Rate of change to positive | |
|---|---|---|
| Group | 2 w | 7 w |
| 1 | 60% (3/5) | 80% (4/5) |
| 2 | 80% (4/5) | 80% (4/5) |
| 3 | 20% (1/5) | 20% (1/5) |
| 4 | 40% (2/5) | 60% (3/5) |

INDUSTRIAL APPLICABILITY

The inactivated JEV particles of the present invention are useful as an adjuvant for enhancing immune response of various vaccines, in particular, a mixed vaccine.

The invention claimed is:

1. A method for preparing a vaccine, the method comprising:
incorporating an inactivated Japanese encephalitis virus, obtained by culture of Vero cells, in the vaccine as an adjuvant wherein the inactived Japenese encephalitis virus is in particles which are present in concentration of 250 ng to 34 µg/mL, and wherein the vaccine is selected from the group consisting of diphtheria/pertussis/tetanus (DPT) vaccine, inactivated polio (IPV) vaccine, HepA vaccine and HepB vaccine.

2. The method of claim 1, wherein the inactivated Japanese encephalitis virus has a particle structure.

3. The method of claim 2, wherein the inactivated Japanese encephalitis virus is comprised in a concentration of 1 to 16 µg/mL.

4. The method of claim 2, wherein the vaccine is a mixed vaccine in which two or more different vaccines are mixed together.

5. The method of claim 4, wherein the inactivated Japanese encephalitis virus is comprised in a concentration of 1 to 16 µg/mL.

6. The method of claim 1, wherein the vaccine is a mixed vaccine in which two or more different vaccines are mixed together.

7. The method of claim 1, wherein the inactivated Japanese encephalitis virus is in particles which are present in a concentration of 1 to 16 µg/mL.

8. A vaccine prepared by the method of claim 7.

9. The vaccine of claim 8, further comprising an aluminum adjuvant.

10. A vaccine prepared by the method of claim 1.

11. The vaccine of claim 10, further comprising an aluminum adjuvant.

12. A method of vaccinating a subject in need thereof comprising administering to said subject an effective amount of a vaccine comprising an inactivated Japenese enecephalitis virus, obtained by a culture of Vero cells, as an adjuvant, and wherein the vaccine is selected from the group consisting of diphtheria/pertussis/tetanus (DPT) vaccine, inactivated polio (IPV) vaccine, HepA vaccine and HepB vaccine.

13. The method of claim 12, wherein the inactivated Japenese encephalitis virus has a particle-like structure.

14. The method of claim 12, wherein the vaccine is a mixed vaccine.

15. The method of claim 12, wherein the inactivated Japanese encephalitis virus is in particles which are comprised in a concentration of 250 ng to 34 µg/mL.

16. The method of claim 12, wherein the inactivated Japanese encephalitis virus is in particles which are comprised in a concentration of 1 to 16 µg/mL.

* * * * *